US007972543B2

(12) United States Patent
Nakajima et al.

(10) Patent No.: US 7,972,543 B2
(45) Date of Patent: Jul. 5, 2011

(54) PROCESS FOR PRODUCING MICROSPHERE WITH USE OF METAL SUBSTRATE HAVING THROUGH-HOLE

(75) Inventors: Mitsutoshi Nakajima, Ibaraki (JP); Taiji Nishi, Tokyo (JP); Seiichi Kanai, Ibaraki (JP); Takenori Kitani, Ibaraki (JP); Motohiro Fukuda, Ibaraki (JP)

(73) Assignees: National Agriculture and Food Research Organization, Tsukuba-shi (JP); Kuraray Co., Ltd., Kurashiki-shi (JP); Mitsutoshi Nakajima, Tsukuba-shi (JP)

( * ) Notice: Subject to any disclaimer, the term of this patent is extended or adjusted under 35 U.S.C. 154(b) by 1087 days.

(21) Appl. No.: 11/577,474

(22) PCT Filed: Oct. 11, 2005

(86) PCT No.: PCT/JP2005/018688
§ 371 (c)(1),
(2), (4) Date: Apr. 18, 2007

(87) PCT Pub. No.: WO2006/043443
PCT Pub. Date: Apr. 27, 2006

(65) Prior Publication Data
US 2008/0061459 A1 Mar. 13, 2008

(30) Foreign Application Priority Data
Oct. 18, 2004 (JP) .................................. 2004-302378

(51) Int. Cl.
*B29B 9/00* (2006.01)
(52) U.S. Cl. ............. 264/14; 264/5; 264/11; 366/176.1; 425/6

(58) Field of Classification Search .................... None
See application file for complete search history.

(56) References Cited

U.S. PATENT DOCUMENTS
6,155,710 A * 12/2000 Nakajima et al. .......... 366/167.1
(Continued)

FOREIGN PATENT DOCUMENTS
CN 1365402 A 8/2002
(Continued)

OTHER PUBLICATIONS
Isao Kobayashi, et al., "Micro Machining Gijutsu Ni Yoru Tanbunsan Micro Sphere Sakuseiyo Kantsugata Silicon Micro Channel No Sakusei", CSJ: The Chemical Society of Japan 79th Spring Meeting, vol. 1, p. 411, 2001.

*Primary Examiner* — Mary Lynn F Theisen
(74) *Attorney, Agent, or Firm* — Oblon, Spivak, McClelland, Maier & Neustadt, L.L.P.

(57) ABSTRACT

An object of the present invention is to provide a process for producing microspheres that are solid microparticles or liquid microparticles for use as an emulsion employed in the food industry, production of medicine and cosmetic etc. or an emulsion for DDS (drug delivery system). The object is attained by a process for producing a microsphere including: separating a disperse phase from a continuous phase by a substrate 1 having a through-hole 7; and extruding the disperse phase into the continuous phase through the through-hole 7, in which the substrate having the through-hole 7 with a width of 0.5 to 500 μm, a depth of 10 μm to 6000 μm and a ratio of the width to the depth of the through-hole 7 of 1 to 1/30 is a metal substrate.

8 Claims, 12 Drawing Sheets

U.S. PATENT DOCUMENTS

| | | | |
|---|---|---|---|
| 6,177,479 B1 * | 1/2001 | Nakajima et al. | 516/73 |
| 6,281,254 B1 * | 8/2001 | Nakajima et al. | 516/53 |
| 7,485,671 B2 * | 2/2009 | Qiu et al. | 516/53 |
| 7,553,434 B2 * | 6/2009 | Kawai et al. | 264/14 |
| 2002/0043731 A1 | 4/2002 | Nakajima et al. | |
| 2002/0157956 A1 | 10/2002 | Ikeda | |

FOREIGN PATENT DOCUMENTS

| | | |
|---|---|---|
| JP | 2 95433 | 4/1990 |
| JP | 2773710 | 4/1998 |
| JP | 2002 119841 | 4/2002 |
| JP | 2003 500205 | 1/2003 |
| JP | 2003 71261 | 3/2003 |

* cited by examiner

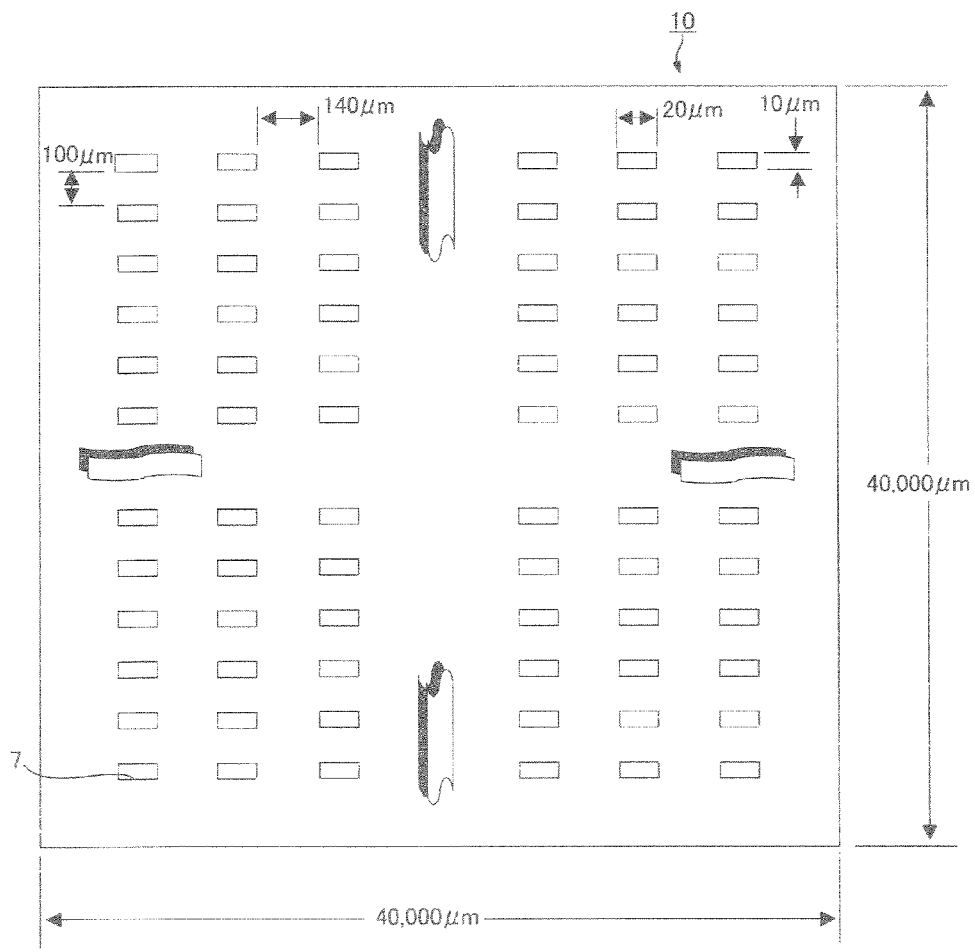
Fig. 4A
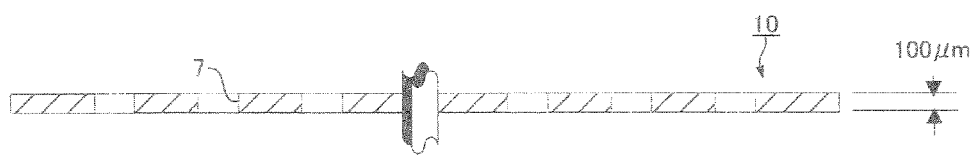
Fig. 4B
|  | (LENGTH × WIDTH) | TOTAL |
|---|---|---|
| THE NUMBER OF THROUGH-HOLES | 300 × 200 | 60,000 |
Fig. 4C

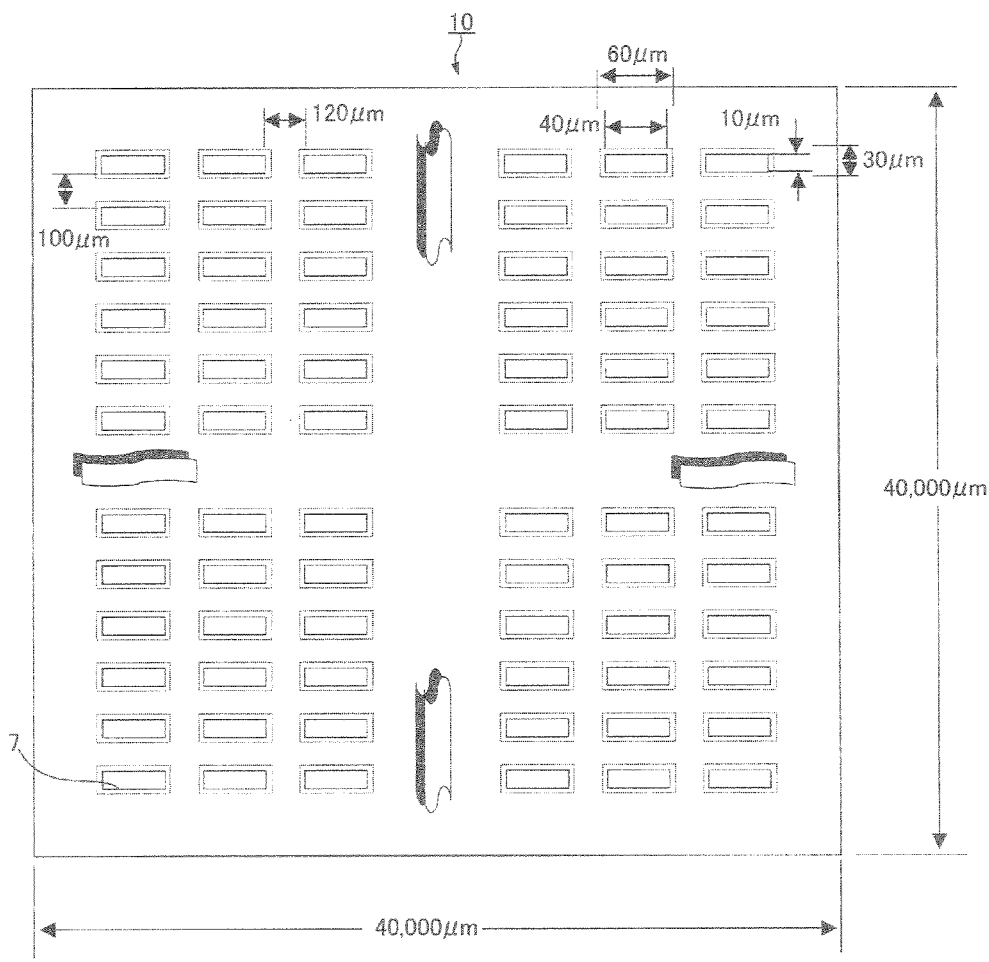
Fig. 8A
Fig. 8B
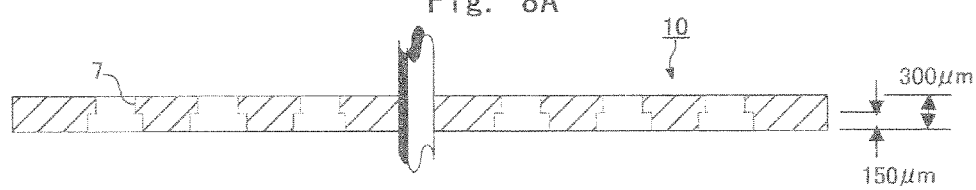
Fig. 8C

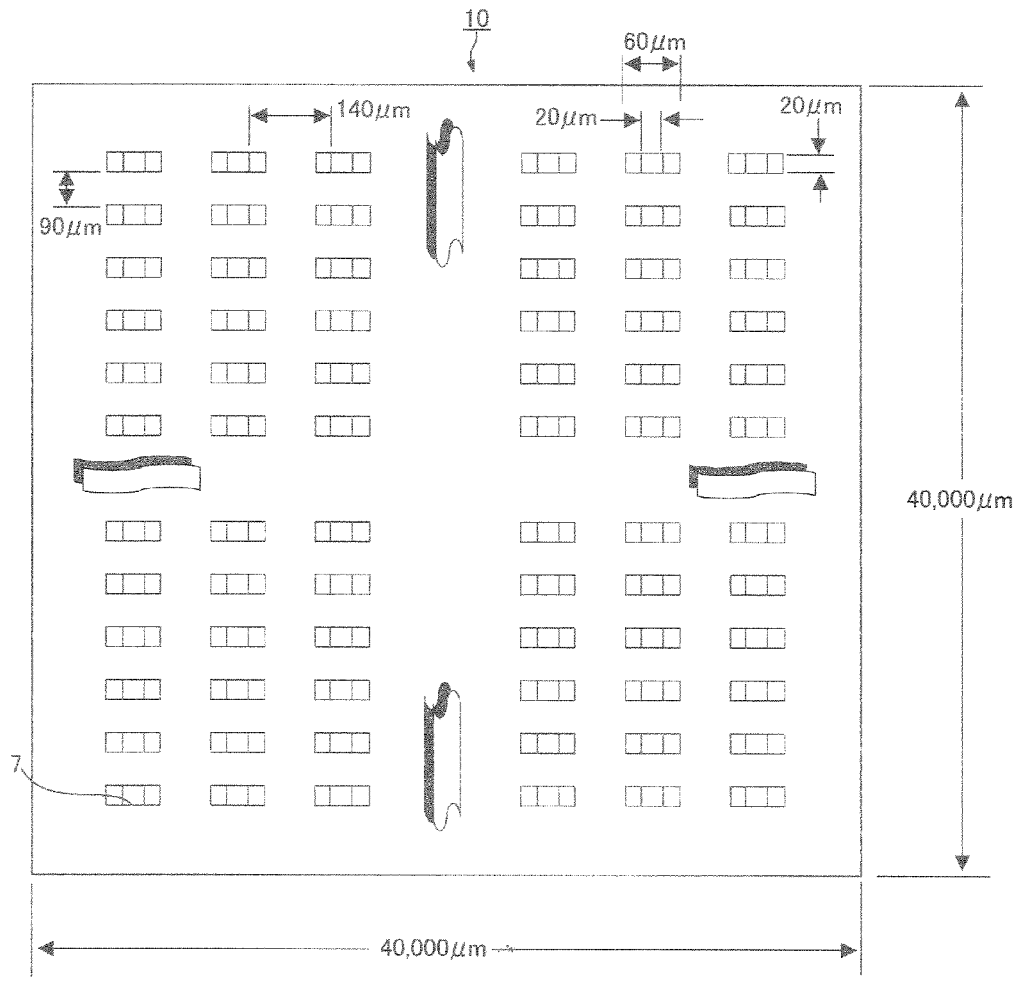
Fig. 9A
Fig. 9B
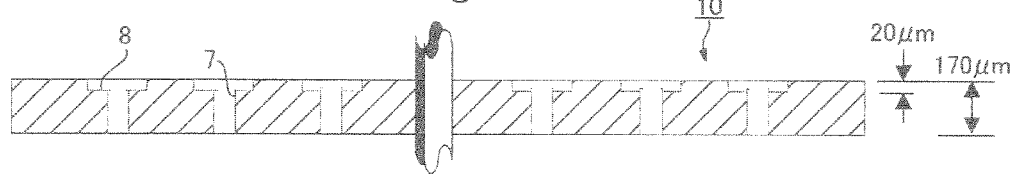
Fig. 9C

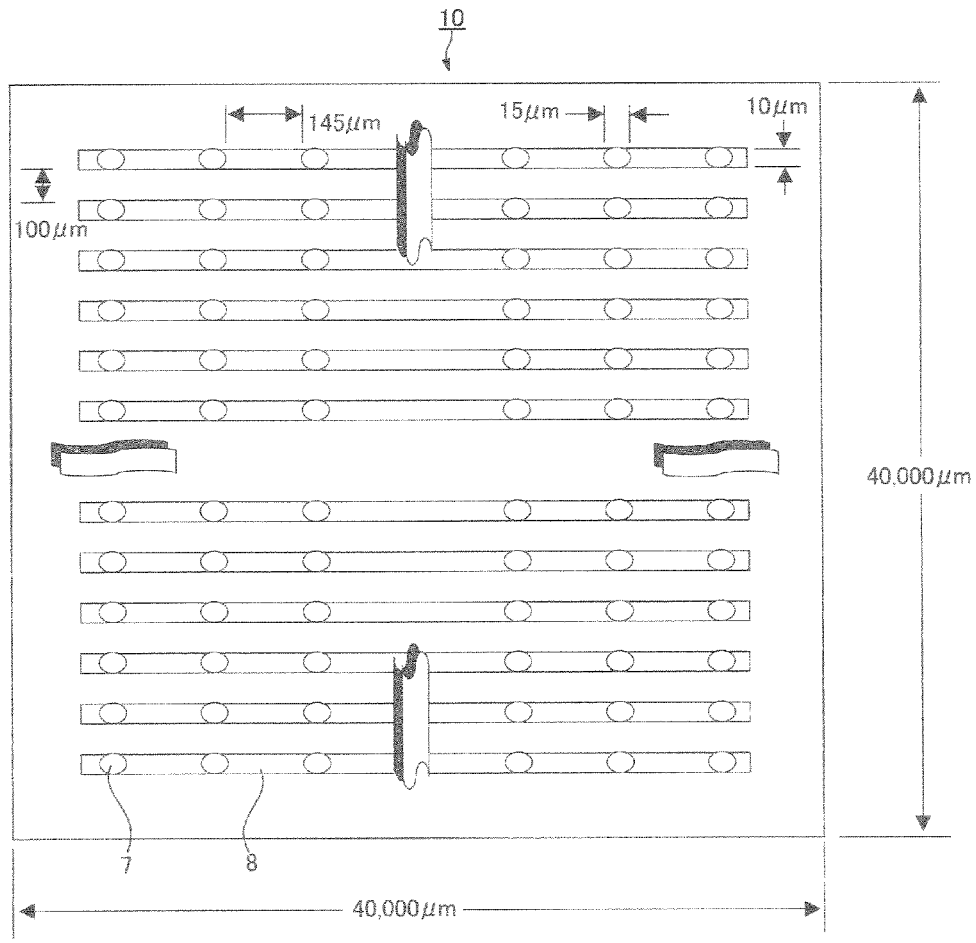
Fig. 10A
Fig. 10B
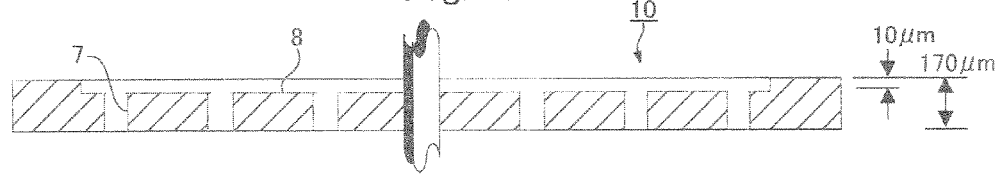
Fig. 10C

PROCESS FOR PRODUCING MICROSPHERE WITH USE OF METAL SUBSTRATE HAVING THROUGH-HOLE

TECHNICAL FIELD

The present invention relates to a process for producing microspheres (microparticles) which are solid microparticles or liquid microparticles for use as, for example, an emulsion employed in the food industry, production of medicine and cosmetic, etc., an emulsion for DDS (drug delivery system), a microcapsule, an ion exchange resin, a chromatography carrier, or the like. In particular, a manufacturing method of a metal substrate having a through-hole of the present invention is useful for a process for producing microspheres, which enables industrial production (mass production) with a view to realizing high fine patterning accuracy, low production costs, and high durability.

BACKGROUND ART

There has been hitherto known a technique of turning a two-phase system such as a system of an aqueous phase and an organic phase a stable state of which is a separated state in thermodynamic terms, into an emulsion that is a metastable state through emulsification.

As a typical example of emulsifying methods, there have been well known an emulsifying method using a mixer, colloid mill, homogenizer, or the like and a dispersing method using ultrasonic as described in "Emulsion Industry" published by Asakura Publishing Co., Ltd. (1971).

The typical emulsion production process is disadvantageous in that disperse-phase particles (microspheres) in a continuous phase largely vary in particle size from one another. To that end, there have been proposed a filtering method using a polycarbonate membrane, a repeatedly filtering method using a PTFE (polytetrafluoroethylene) membrane, and a method of supplying a target material to a continuous phase through a porous glass membrane having uniform pores to thereby produce a homogeneous emulsion (see Patent Document 1).

The filtering method using a polycarbonate membrane or PTFE membrane has a problem in that an emulsion cannot be produced beyond a pore size of a membrane and emulsion particles smaller than the pore size cannot be fractionated in principle. Therefore, this method is unsuitable especially for production of an emulsion having a large particle size.

Further, in the method using a porous glass membrane having uniform pores, if an average pore size of the membrane is small, a pore size distribution is small, so a homogeneous emulsion can be produced. However, if the average pore size is large, the pore size distribution becomes large, making it difficult to produce a homogeneous emulsion.

To solve the above problems, there has been proposed a process for producing a microsphere, which separates a disperse phase from a continuous phase by a partition having through-holes and applies to the disperse phase a pressure larger than that applied to the continuous phase to thereby extrude the disperse phase into the continuous phase to obtain microspheres, in which shear force is nonuniformly applied to the disperse phase extruded into the continuous phase through the through-holes to complete the microspheres (see Patent Document 2).

However, a substrate prepared by subjecting a silicon substrate to wet or dry etching based on the semiconductor microfabrication technique proposed in the specification and embodiments of the above publications is not impractical because 1) the substrate tends to get damages when in use or washing, 2) the silicon substrate costs high, and 3) through-hole width accuracy is low.

Assuming that a through-hole is formed in a silicon substrate, a substrate having the thickness of 0.1 mm to 0.3 mm is generally used. As the number of through-holes (through-hole area) is increased, mechanical strength is considerably lowered. As a result, there is a fear that the substrate is broken at the time of producing a microsphere. Thus, this processing method is not practical.

In addition, it is highly possible that the substrate is broken upon ultrasonic cleaning for reuse, for example.

The wet etching is not a precise process because high through-hole width accuracy is not secured depending on the progress of under etching below a masking material.

In contrast to wet etching, dry etching is a technique developed out of a pattern forming process of a silicon semiconductor. The application of dry etching to various electronic components with various kinds of plasma sources or a compound semiconductor has been under study. However, this process excels in microfabrication property, but an etching rate is as low as 500 to 2,000 nm/min. Thus, in the case of processing a target material with the shaping depth of, for example, 0.1 mm, a process time not Less than 50 minutes is required, so this process is not a low-cost process with high productivity.

Since the etching rate is low, reducing a substrate thickness to form a through-hole increases the possibility of breakage when in use or cleaning.

Another production process as a possible solution to the above problems is a laser processing technique. However, a general carbon dioxide laser widely used for cutting a metal or resin material or forming a through-hole has as large a laser spot size as 500 μm and thus is unsuitable for formation of small through-holes under present circumstances. In addition, there is a problem in that a process depth decreases as the spot size is more reduced with a condenser lens.

If a YAG laser having the minimum laser spot size of 30 to 50 μm is selected, the minimum possible through-hole diameter of 50 to 100 μm is realized, but laser power and directivity are low, so the upper limit of the process depth is 10 to 50 μm. Under present circumstances, the YAG laser is applied to formation of a printed wiring board or the like (see Patent Document 3).

To attain both of a small laser spot size and large process depth, laser pulse irradiation has been known. In particular, a femtosecond laser realizes the process depth of 50 μm or more with the minimum through-hole diameter of 10 to 50 μm. However, a process using the femtosecond laser is disadvantageous in that a femtosecond laser oscillator has not yet come into widespread use on an industrial scale. In addition, the oscillator is as expensive as about 100,000,000 yen per oscillator, which increases a production cost of a metal substrate having a through-hole. Moreover, as the number of through-holes of a metal substrate increases, a requisite processing period increases, and a price of a device for scanning a large area increases. Thus, its efficiency would be lowered on practical side as well.

Another production process as a possible solution to the above problems is a precision machining technique employing a precision cutting tool. However, the minimum possible bit diameter of the precision cutting tool is Φ100 μm, so it is impossible to form a through-hole with a diameter smaller than the bit diameter. In addition, machining is executed on the hole basis. Thus, it takes several hours to form several tens of thousands to several hundreds of thousand of through-holes, and its cost increases. Further, in the case of processing a large area of Φ4 inches or more (diameter of 100 mm), the precision cutting tool is worn out, resulting in a high cost.
[Patent Document 1]
Japanese Unexamined Patent Application Publication No. 2-95433
[Patent Document 2]
Japanese Patent No. 3511238
[Patent Document 3]
Japanese Patent No. 2773710

DISCLOSURE OF THE INVENTION

Problems to be Solved by the Invention

The wet etching process or dry etching process for a silicon substrate based on the semiconductor microfabrication technique or the conventional manufacturing method of a metal substrate having a through-hole has problems in that intended through-hole width and depth cannot be obtained, the substrate is easily damaged when in use or cleaning, a material cost of the silicon substrate is high, and a metal substrate having desired through-hole width and depth cannot be manufactured with high productivity.

The present invention has been made with a view to solving the above problems. It is accordingly an object of the present invention to provide a process for producing a microsphere with use of a metal substrate having desired through-hole width and depth.

Another object of the present invention is to provide a microsphere produced with use of a metal substrate having desired through-hole width and depth.

Another object of the present invention is to provide a manufacturing method of a microsphere-production metal substrate having desired through-hole width and depth, and a microsphere-production metal substrate manufactured by the method.

Another object of the present invention is to provide a device for producing a microsphere with use of the microsphere-production metal substrate as a substrate having a through-hole.

Means for Solving the Problems

The present inventors have made extensive studies to solve the above problems and thereby found that the above problems can be solved by a process for producing a microsphere including: separating a disperse phase from a continuous phase by a substrate having a through-hole; and extruding the disperse phase into the continuous phase through the through-hole, in which the substrate is a metal substrate having predetermined width and depth, and the present invention has been accomplished.

That is, the present invention provides a process for producing a microsphere including separating a disperse phase from a continuous phase by a substrate having a through-hole; and extruding the disperse phase into the continuous phase through the through-hole, in which at least one metal substrate having a through-hole with a width of 0.5 to 500 μm, a depth of 10 μm to 6000 μm, and a ratio of the width to the depth of the through-hole (width/depth) of 1 to 1/30 (1/1 to 1/30) is used as the substrate.

Further, in the process for producing a microsphere according to the present invention, it is preferred that the metal substrate be subjected to chemical surface treatment and/or physical surface treatment, the through-hole formed in the metal substrate have a multistage structure, a recess be formed around an opening of the through-hole on the side where the microsphere is formed, a plurality of metal substrates having a through-hole be prepared, the metal substrate have through-holes of two or more different shapes, and a support plate supporting the substrate be formed on at least one side of the metal substrate.

Further, the present invention provides a microsphere produced by the process for producing a microsphere.

Further, the present invention provides a manufacturing method of a metal substrate having a through-hole for use in the producing a microsphere, including: a resist pattern formation step of forming a resist layer on a resist-formation substrate and subjecting the resist-formation substrate to exposure and development, or exposure, heat treatment, and development to form a resist pattern having a through-hole shape; and a metal substrate formation step of depositing metal through plating based on the resist pattern and then peeling the resist-formation substrate, and removing the resist pattern with a developer to form a metal substrate.

Furthermore, in the manufacturing method of a metal substrate according to the present invention, it is preferred that the resist pattern formation step include forming a resist layer by use of a conductive resist-formation substrate and subjecting the conductive resist-formation substrate to exposure and development, or exposure, heat treatment and development, the resist pattern formation step include repeating formation of a resist layer a plurality of times and executing exposure and development, or exposure, heat treatment, and development one or more times until the total resist pattern thickness reaches a height of the through-hole, to form a resist pattern having a through-hole shape, the method further include: a mask alignment step of adjusting positions of mask patterns of each layer such that the mask patterns of each layer are aligned upon exposure with a mask if formation of a resist layer is repeated a plurality of times and exposure and development, or exposure, heat treatment, and development are executed one or more times in the resist pattern formation step, if the formation of a resist layer is repeated a plurality of times in the resist pattern formation step, resist materials of different exposure sensitivities be used for resist layers, and in the resist pattern formation step, a light source for the exposure be UV light or laser light.

Further, the present invention provides a metal substrate having a through-hole manufactured by the manufacturing method.

Further, the present invention on provides a device for producing a microsphere, including: a case including a first plate, a substrate having a through-hole, and a second plate, which are spaced out in the case; a first channel through which a disperse phase flows and which is formed between the first plate and the substrate having a through-hole; a second channel through which a bed including a continuous phase and a microsphere flows and formed between the substrate having a through-hole and the second plate, wherein the substrate is a metal substrate having a through-hole with a width of 0.5 to 500 μm, a depth of 10 μm to 6000 μm, and a ratio of the width to the depth of the through-hole (width/depth) of 1 to 1/30 (1/1 to 1/30).

Furthermore, in the device for producing a microsphere according to the present invention, at least a part of the first plate and/or the second plate is formed of a transparent material.

Advantages of the Invention

According to the present invention, it is possible to provide a process for producing a microsphere with use of a metal substrate having desired through-hole width and depth. In addition, according to the present invention, it is possible to provide a microsphere produced by use of a metal substrate having desired through-hole width and depth. Further, according to the present invention, it is possible to provide a manufacturing method of a microsphere-production metal substrate having desired through-hole width and depth, and a microsphere-production metal substrate manufactured with the manufacturing method. Furthermore, according to the present invention, it is possible to provide a device for producing a microsphere, which employs the microsphere-production metal substrate as a substrate having a through-hole.

For example, the present invention enables production of microspheres (microparticles) which are solid microparticles or liquid microparticles for use as an emulsion employed in the food industry, production of medicine and cosmetic, etc., an emulsion for DDS (drug delivery system), a microcapsule, an ion exchange resin, a chromatography carrier, or the like in such a manner that demands for high fine patterning accuracy, low production costs, and high durability are satisfied and industrial production (mass production) is realized.

In particular, if the present invention is applied to production of mayonnaise, chocolate, margarine, fat spread, or the like, disperse-phase particles can be uniformly formed with small size, separation hardly occurs even during long-term storage, and the texture is improved by use of a microsphere of the present invention. The present invention realizes industrial production (mass production) of the microsphere.

BRIEF DESCRIPTION OF THE DRAWINGS

FIG. 4A shows an outer appearance of a through-type metal structure manufactured through a manufacturing process of FIGS. 1A to 1F;

FIG. 4B shows an outer appearance of a through-type metal structure manufactured through a manufacturing process of FIGS. 1A to 1F;

FIG. 4C shows an outer appearance of a through-type metal structure manufactured through a manufacturing process of FIGS. 1A to 1F;

FIG. 8A shows an outer appearance of a through-type metal substrate manufactured through a manufacturing process of FIGS. 2A to 2H;

FIG. 8B shows an outer appearance of a through-type metal substrate manufactured through a manufacturing process of FIGS. 2A to 2H;

FIG. 8C shows an outer appearance of a through-type metal substrate manufactured through a manufacturing process of FIGS. 2A to 2H;

FIG. 9A shows an outer appearance of a through-type metal substrate manufactured through a manufacturing process of FIGS. 2A to 2H;

FIG. 9B shows an outer appearance of a through-type metal substrate manufactured through a manufacturing process of FIGS. 2A to 2H;

FIG. 9C shows an outer appearance of a through-type metal substrate manufactured through a manufacturing process of FIGS. 2A to 2H;

FIG. 10A shows an outer appearance of a through-type metal substrate manufactured through a manufacturing process of FIGS. 2A to 2H;

FIG. 10B shows an outer appearance of a through-type metal substrate manufactured through a manufacturing process of FIGS. 2A to 2H;

FIG. 10C shows an outer appearance of a through-type metal substrate manufactured through a manufacturing process of FIGS. 2A to 2H.

Figure 1A:
FIG. 1A is a schematic diagram of a manufacturing process of a metal substrate having a through-hole according to the present invention.

DESCRIPTION OF REFERENCE NUMERALS 1 substrate
2 resist layer 3 mask
4 resist pattern
5 conductive film
6 metal structure
7 through-hole
10 metal substrate having a through-hole

BEST MODES FOR CARRYING OUT THE INVENTION

Hereinafter, an embodiment of the present invention is described in detail.

A through-hole size of a metal substrate having a through-hole of this embodiment is preferably selected in accordance with its application to an emulsion employed in the food industry, production of medicine and cosmetic, etc., an emulsion for DDS (drug delivery system), a microcapsule, an ion exchange resin, a chromatography carrier, or the like.

If a shear force is nonuniformly applied to a disperse phase extruded into a continuous phase, the disperse phase is readily separated into a rough microsphere, making it possible to produce microspheres of uniform particle size. The production of microspheres of uniform particle size is attained by forming an opening of a through-hole into a slot shape or other such distorted shapes. That is, when the disperse phase is extruded from the through-hole, distribution occurs along the direction of force applied vertically to an interface and from an outer side to an inner side, and an interface between a disperse phase and a continuous phase becomes unstable, which promotes shearing along the interface to produce fine and homogeneous microspheres.

Hence, it is preferred to design an opening for extruding a disperse phase to a continuous phase as an elliptical or rectangular shape rather than a circular or circle-like shape and a square or square-like shape in terms of ease of separation of a disperse phase from opening. A ratio between the short size (short diameter) and the long side (long diameter) of a rectangular shape (elliptical shape) is preferably 1:1 to 1:20, more preferably 1:2 to 1:10.

If the microsphere is intended for an emulsion or the like, for example, a disperse phase and a continuous phase are both liquid phases. If the microsphere is intended for spray drying, a liquid phase is used as a disperse phase, and a gas phase is used as a continuous phase.

A through-hole of a metal substrate having a through-hole is formed based on a technique of producing a stamper (disk) having uneven patterns for the production of recording media such as a laser disk and a minidisk or optical produces such as light guide. According to this technique, a through-hole can be formed into an extremely small size with high accuracy. The width of a through-hole is preferably selected from a range of 0.5 to 500 μm, more preferably 1 to 250 μm in accordance with its application. Regarding the through-hole width, for example, the width refers to the diameter for a circular through-hole, refers to the short diameter for an elliptical through-hole, and refers to the short side for a rectangular through-hole.

The depth of a through-hole is preferably selected from a range of 10 μm to 6000 μm, more preferably 30 μm to 3000 μm.

A ratio of width to depth of a through-hole (width and depth) is preferably selected from a range of 1 to 1/30, more preferably 1 to 1/20.

A type of an objective microsphere may be changed in accordance with whether a metal substrate having a through-hole has hydrophilic property or hydrophobia property. That is, if a hydrophilic plate is employed, an O/W type (oil-in-water type) microsphere can be produced. If a hydrophobia plate is used, a W/O type (water-in-oil type) microsphere can be produced. A processing for imparting hydrophilic or hydrophobia property to the metal substrate having a through-hole can be carried out by depositing an organic or inorganic material on the metal substrate surface through plating or the like.

In general, techniques of improving wettability of the material surface are roughly classified into a chemical treatment technique and a physical treatment technique. Examples of the chemical treatment technique include chemical treatment, solvent treatment, coupling agent treatment, monomer coating, polymer coating, inorganic material coating, steaming, surface grafting, electrochemical treatment, and anodic oxidation. On the other hand, examples of the physical treatment technique include UV irradiation, plasma contact treatment, plasma jet treatment, plasma polymerization, vapor deposition polymerization, thermal oxidation, ion beam deposition, and mechanical treatment.

In a process for producing a microsphere with use of a metal substrate having a through-hole, if the through-hole has a multistage structure, microsphere production efficiency can be further increased.

To stably produce microspheres, when a disperse phase is sheared at the interface, a continuous phase around the interface of an opening needs to be moved/supplied to the interface. Thus, it is necessary that a certain amount of continuous phase exists around the interface. In addition, a continuous phase should be supplied to collect the produced microsphere, and a flow rate of the continuous phase is changed to thereby arbitrarily set the proportion of disperse phase in an emulsion.

To increase microsphere production efficiency, it is necessary to positively supply the continuous phase around the interface of an opening at the time of shearing the disperse phase at the interface. As a method of positively supplying a continuous phase to the interface of an opening, an opening-side dimension of a through-hole is set larger than an inner-side hole size to thereby positively supply the continuous phase to increase microsphere production efficiency.

Further, the opening-side dimension of a through-hole is set larger than the inner-side hole size to thereby supply a continuous phase beyond the interface of the opening, and positively shear the disperse phase at the interface to further increase microsphere production efficiency.

If the opening-side dimension of a through-hole is set larger than the inner-side hole size, the disperse phase is extruded into the continuous phase due to an effect of positively shearing the disperse phase at the interface. The inner-side opening near the interface may take a circular or circle-like shape or a square or square-like shape.

In the process for producing a microsphere with use of a metal substrate having a through-hole, if a recess is formed around the microsphere formation side, the microsphere production efficiency can be further enhanced. The recess is formed around an opening of a through-hole on the side where a microsphere is formed to thereby positively supply a continuous phase and increase microsphere production efficiency.

Assuming that the entire depth of the through-hole is as small as 50 μm, for example, if the opening-side dimension is larger than the inner-side hole size, a disperse phase can be only supplied for producing a microsphere over a very small area. As a result, microspheres cannot be stably produced in some cases. Therefore, it is desirable to form a recess around the opening of a through-hole.

Figure 3A:
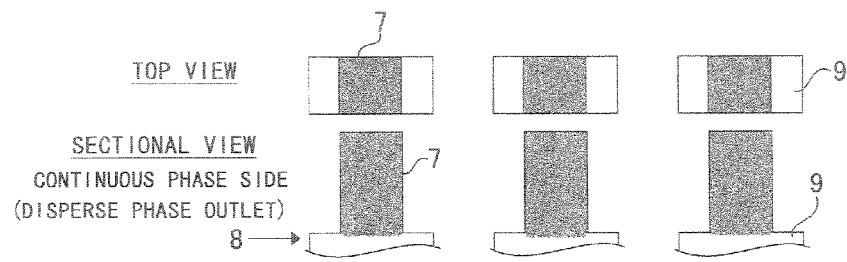
FIG. 3A is a schematic diagram of a through-hole formed into a multistage structure for improving microsphere production efficiency according to the present invention.
Figure 3B:
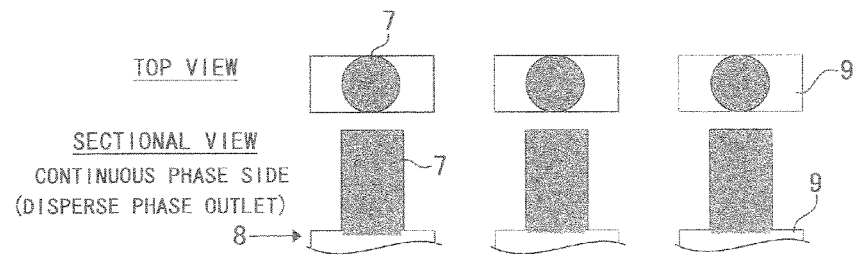
FIG. 3B is a schematic diagram of a through-hole formed into a multistage structure for improving microsphere production efficiency according to the present invention.
Figure 3C:
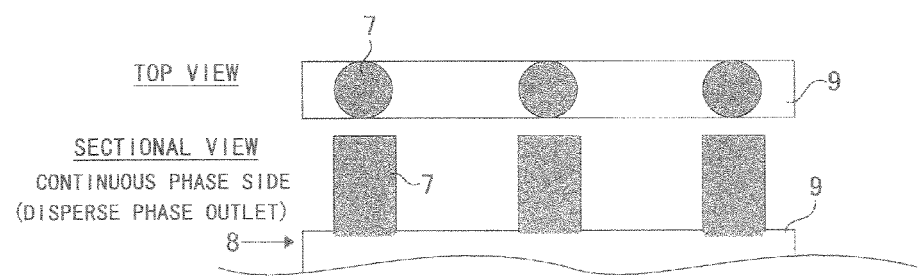
FIG. 3C is a schematic diagram of a through-hole formed into a multistage structure for improving microsphere production efficiency according to the present invention.

FIGS. 3A to 3E show structural examples of a through-hole formed into a multistage structure or a through-hole shaped such that a recess is formed around an opening on the microsphere formation side for improving microsphere production efficiency. A through-hole 7 of FIG. 3A is rectangular in section, and the through-hole 7 of FIGS. 3B and 3C is circular in section.

FIGS. 3A to 3C show examples of the multistage structure. However, there is no particular limitation on the shape of the through-hole 7. For example, the through-hole may be a rectangular circular, or elliptical shape or a combination thereof. Further, there is no particular limitation on the shape of the through-hole 7 on a continuous phase side (disperse phase outlet) 8. However, it is important to set its dimension larger than the size of the through-hole 7 below (behind) the outlet with a view to attaining higher particular isolation efficiency. For example, if the size of the through-hole 7 on the continuous phase side (disperse phase outlet) 8 is set a little larger than the size of the through-hole below (behind) the outlet, production efficiency can be improved. As for a shape of the through-hole on the continuous phase side (disperse phase outlet) 8, the through-hole may be continuous with an adjacent through-hole as shown in FIG. 3C. In this case, a continuous phase can be supplied more easily to the through-hole side, and the microsphere production efficiency can be dramatically improved. Further, there is no limitation on the multistage structure of the through-hole 7 unless otherwise specified in manufacturing of a metal substrate, and a two-stage or three or more stage structure as shown in FIG. 3C may be used.

Figure 3D:
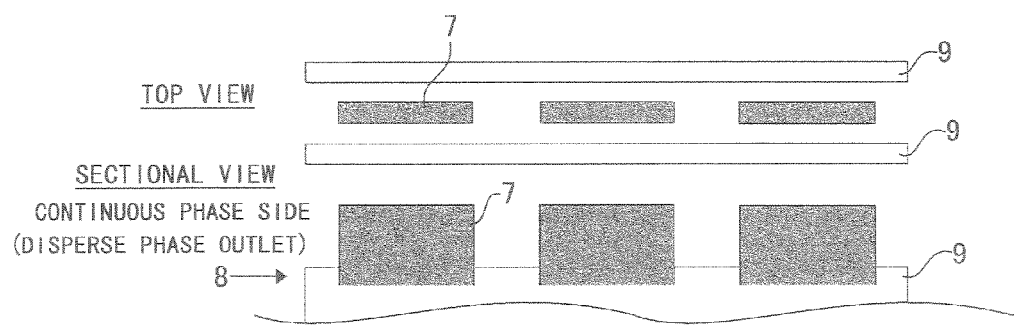
FIG. 3D is a schematic diagram of a through-hole shaped such that a recess is formed around the microsphere formation side for improving microsphere production efficiency according to the present invention.
Figure 3E:
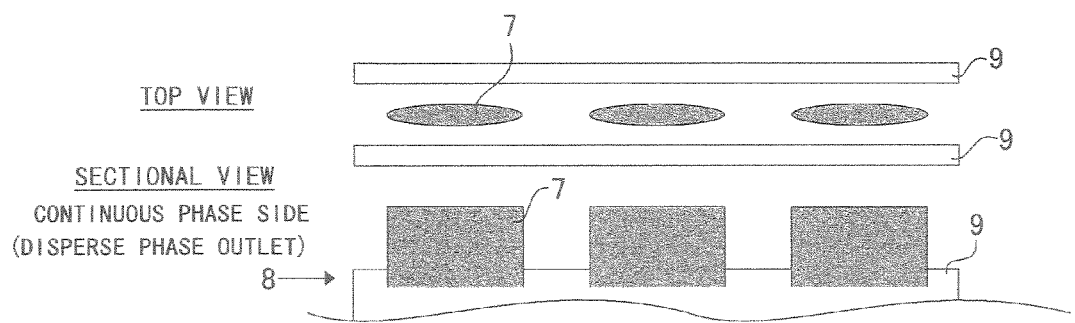
FIG. 3E is a schematic diagram of a through-hole shaped such that a recess is formed around the microsphere formation side for improving microsphere production efficiency according to the present invention.

According to the present invention, as shown in FIGS. 3D and 3E, the formation of a recess around the continuous phase side (disperse phase outlet) 8 as the microsphere formation side is expected to further improve the microsphere production efficiency. For example, in the example of FIG. 3D, rectangular concave portions (that is, recesses) 9 are formed on both sides of plural rectangular through-holes. In the example of FIG. 3E, rectangular concave portions (that is, recesses) 9 are formed on both sides of plural oblong through-holes 7. However, the shape and size of the recess 9 are not particularly limited and may be appropriately changed in accordance with the arrangement of the through-holes 7. Regarding the formation of recesses, the recesses can be formed near the through-holes 7 unless the shape of the through-hole 7 is not thereby changed. For example, the recesses on both sides of the through-hole 7 may be coupled.

In the process for producing a microsphere with use of a metal substrate having a through-hole, if plural metal substrates having a through-hole are prepared, the microsphere productivity can be increased.

In particular, to meet a demand for production of 1 to 100 tons/year on the industrial scale, the demand is satisfied by increasing the area and number of metal substrates having a through-hole.

If the metal substrate has through-holes of two or more different shapes, the microsphere production efficiency can be increased. Assuming that a single metal substrate having a through-hole has only one type of through-hole, microspheres of just one particle size can be only produced. If microspheres of different particle sizes are necessary in actual use, for example in industrial use, the microsphere production efficiency can be increased by use of a metal substrate having through-holes of two or more different shapes.

In a device for producing a microsphere with use of a metal substrate having a through-hole, a support plate for supporting the metal substrate is placed on at lease one side of the metal substrate having a through-hole to increase the microsphere productivity.

If the depth of the metal substrate having a through-hole (metal substrate thickness) is as small as 40 μm to 80 μm, for example, an application range of a pressure for producing a microsphere is narrowed. If a solution sending pressure for a disperse phase increases beyond the upper limit, the disperse phase is supplied too fast to shear at the interface, with the result that the disperse phase gushes into the continuous phase. The application range of a pressure for producing a microsphere can be widened by bonding the manufactured metal substrate to a single support plate having similar through-holes or a laminate of the plural support plates. The shape of the microsphere varies depending on the shape and dimension of an opening at the interface, so the size of the through-hole on the support plate side may be similar to, or larger or smaller than that of the metal substrate.

Further, the provision of the support plate for supporting the metal substrate enhances metal substrate handling property and durability.

The width, shape, and height of a fine convex pattern formed in a resist pattern formation step correspond to the width, shape, and height of the through-hole in a metal substrate having a through-hole.

A fine convex resist pattern formation technique is an advanced one of the technique of producing a stamper (disk) having uneven patterns that are extremely fine with high dimension accuracy for the production of recording media such as a laser disk and a minidisk or optical produces such as light guide.

In the step of forming a through-type metal structure through plating based on the fine convex resist pattern, a deposition time of the metal structure through plating is controlled to thereby obtain the through-type metal structure with a desired thickness. The thus-produced metal substrate having a through-hole has extremely high mechanical strength and durability under actual use or repeated cleaning.

The number of through-holes formed in the metal substrate is not particularly limited unless lowering the strength. The number of through-holes is generally 1 to 1,000,000/cm$^2$, preferably 1 to 500,000. For example, a through-hole area of the outer dimension of 4 cm (length)×4 cm (width), 100,000 or more through-holes can be formed at a time. Even if fine convex patterns formed in the resist pattern formation step are arranged with high density in accordance with the application, and 200,000 or more through-holes are formed, a metal substrate that can keep high durability and practical utility under actual use or repeated cleaning is obtained.

Further, if a resist pattern having as large an area as Φ5 inches or more (diameter of 125 mm) is formed and the metal structure is deposited through plating, plural through-type metal structures can be produced and a production cost can be considerably saved.

To manufacture a metal substrate of a desired through-hole, it is necessary to improve the fine convex resist pattern formation technique for production of recording media such as a laser disk or a minidisk. In the production of the recording media or the like, the fine convex resist pattern has a height as small as 1 to 3 μm, so no particular problem arises.

However, in the case of forming a fine resist pattern having the width of 3 μm and the height of 10 μm or more, for example, there arises a problem in that a fine convex resist pattern of an upper layer is deformed or broken in some cases at the time point when development proceeds from the upper layer to a lower layer. Further, an aspect ratio (ratio of height to width) increases in the developing step, resulting in another problem that the fine convex resist pattern falls down in some cases.

To overcome the problem that a fine convex resist pattern of an upper layer is deformed or broken at the time point when development proceeds from the upper layer to a lower layer in the developing step, a developer solubility in the upper layer is set lower than that of the lower layer upon repeating the formation and exposure of a resist layer plural times until the resist layer thickness reaches the desired thickness in the fine convex resist pattern formation step. In this way, the above problem is solved.

If a heat amount (temperature and period) necessary for baking the upper resist layer is set larger than the lower resist layer, the solubility of the upper layer is lower than that of the lower layer. For example, the lower layer is baked with a hot plate, and then the upper layer is baked with a clean oven (hot air dryer) which enables selective baking.

In the case of using a photosetting resist (negative resist) as a resist material, an exposure amount of the upper layer is set larger than that of the lower layer to thereby make the solubility of the upper layer lower than that of the lower layer. In the case of using a chemically-amplified negative resist, an exposure amount of the upper layer is set larger than that of the lower layer, and in addition, a heat treatment amount (temperature and period) of the upper layer after the exposure is set larger than that of the lower layer.

To overcome the problem that an aspect ratio (ratio of height to width) increases in the developing step and thus the fine convex resist pattern falls down, in addition to the above method, the pattern shape (width) of the lower layer is set somewhat larger than that of the upper layer upon repeating the formation and exposure of a resist layer plural times. In this way, it is possible to prevent the fine convex resist pattern from falling down.

To set the pattern shape (width) of the lower layer somewhat larger than that of the upper layer lower layer, for example, there is a UV parallel light exposure process that executes proximity exposure under such conditions that a distance between the upper surface of the lower layer and a mask is 1 to 50 μm, thereby making the pattern shape (width) of the lower layer larger than the actual mask pattern owing to the light scattering. Alternatively, a mask of a size larger than that for the upper layer is used for exposure of the lower layer.

The metal substrate having a through-hole of this embodiment is produced through the fine convex resist pattern formation step including:
(a) formation of resist layer on substrate
(b) resist layer exposure with mask
(c) heat treatment on resist layer
(d) development
and
(e) deposition of metal structure through plating
(f) removal of resist in accordance with the fine convex resist pattern formed on the substrate.
   (a) Formation of Resist Layer on Substrate is Described Below.

There is no limitation on a method of forming a resist layer on the substrate. In general, spic coating, dipping, a roll process, and bonding of dry film resists may be used. Among those, the spin coating is a technique of applying a resist on a rotating glass substrate, which has an advantage in that a resist can be applied onto a glass substrate having the diameter larger than of 300 mm with high flatness. In light of the high flatness, the spin coating is preferred.

Usable resists are classified into two types: a positive resist and a negative resist. In either type, an exposable resist depth varies depending on a sensitivity of a resist and exposure conditions. Thus, if a UV exposure device is used, for example, it is desirable to select an exposure period and UV power in accordance with resist thickness and sensitivity.

In the case of using a wet resist, a predetermined resist thickness can be obtained through spin-coating, for example, with a method of changing the rpm for spin coating or a method of adjusting viscosity.

According to the method of changing the rpm for spin coating, the spin coater rpm is appropriately set to obtain a desired resist thickness. According to the method of adjusting the viscosity, since there is a fear that the flatness lowers as the resist thickness or coating area increases, the viscosity is adjusted in accordance with the requisite flatness in actual use.

For example, as for the spin coating, the resist layer thickness obtained through one coating is preferably in 10 to 50 μm, more preferably 20 to 50 μm from the viewpoint of keeping high flatness. A desired resist layer thickness can be obtained with the flatness kept high by forming plural resist layers.

(b) Resist Layer Exposure with Mask is Described Next.

The specifications of a mask are not particularly limited, and an emulsion mask, a chromium mask, or the like can be used. In the resist pattern formation step, the dimension and accuracy vary depending on which mask is used, and the dimension and accuracy in turn influence the metal substrate having a through-hole. Therefore, the mask dimension and dimensional accuracy should be specified for manufacturing a metal substrate having a through-hole with desired dimension and accuracy. There is no particular limitation on how to improve the mask dimensional accuracy. For example, a light source with the wavelength shorter than that of a laser light source may be used to form a mask pattern, but a high plant cost is necessary and mask formation costs high. Thus, it is desirable to appropriately specify the dimension and accuracy in accordance with an accuracy required of the through-type metal structure in actual use.

As a mask material, quartz glass is preferred in terms of thermal expansion coefficient and UV absorption property but is relatively expensive. Thus, it is desirable to appropriately set the accuracy and dimension in accordance with an accuracy required of the through-type metal structure in actual use.

The light source for exposure is preferably UV or laser light the plant cost of which is low. Synchrotron orbital radiation enables the large exposure depth but requires a high plant cost. Thus, although the through-type metal structure is high in price and impractical in industrial term, the synchrotron orbital radiation may be employed.

Exposure conditions such as an exposure period and an exposure intensity vary depending on resist layer material and thickness etc. Hence, it is desirable to appropriately set the conditions in accordance with a target pattern. In particular, the etching conditions influence the width, size, and dimensional accuracy of a through-hole, so it is important to adjust the exposure conditions. Further, the upper limit of the exposure depth varies depending on a resist type. If a UV exposure device is used, for example, it is desirable to select an exposure period and UV power in accordance with the resist thickness and sensitivity.

(c) Heat Treatment on Resist Layer is Described Next.

As heat treatment after exposure, heat treatment called annealing for adjusting a resist pattern shape is known.

This example is directed to chemical crosslinking, and heat treatment is executed only in the case of using a chemically-amplified negative resist. The chemically amplified negative resist mainly has a two-component system or three-component system. Exposure light causes ring-opening of an epoxy group at the terminal of the chemical structure, and then heat treatment is carried out to cause a crosslinking reaction. The crosslinking reaction proceeds due to heat treatment in several minutes under the conditions that preset temperature is 100☐ for the thickness of 100 μm, for example.

(d) Development is Described Next.

It is preferable to use a predetermined developer suited for a target resist upon development. Development conditions such as development period and temperature, and a developer concentration are desirably adjusted as appropriate in accordance with the resist thickness or pattern shape. For example, if the development period is too long, the finished size becomes smaller than a predetermined fine convex resist pattern size. Thus, it is preferable to appropriately set the conditions.

(e) Metal Structure Deposition Through Plating is Described Next.

The metal structure deposition is a step of depositing metal in accordance with a resist pattern formed in the fine convex resist pattern formation step, and forming the metal structure into a concave shape along the fine convex resist pattern to thereby complete the metal structure.

In this step, a conductive film is previously formed in accordance with a fine convex resist pattern. There is no particular limitation on how to form the conductive film, and evaporation and sputtering are preferably used. Conceivable conductive materials for the conductive film include gold, silver, platinum, copper, nickel, and aluminum.

After the formation of the conductive film, metal is deposited through plating in accordance with the fine convex pattern to form the metal structure. There is no particular limitation on a plating method for depositing metal, and electrolytic plating, nonelectrolytic plating, and the like can be employed, for example In the nonelectrolytic plating, a conductive film can be omitted. Any metal can be used without particular limitations, and nickel, a nickel-cobalt alloy, copper, and gold can be used. In light of economic efficiency/durability, nickel is preferred.

If the metal structure is deposited through plating up to the same thickness as the fine convex resist pattern, a period necessary for subsequent dissolution for forming the through-type structure or necessary for polishing can be reduced.

The metal structure may be polished in accordance with its surface condition. However, there is a possibility that dirt adhere to the finished product, so it is preferable to perform ultrasonic cleaning after polishing. The metal structure deposited through plating is separated from the fine convex resist pattern.

(f) Removal of Resist is Described Next.

The removal of resist is carried out to remove the fine convex resist pattern on the metal structure. A resist is preferably removed with a predetermined solution suited for the resist. A photocrosslinked negative resist is supposed to be slightly soluble. To overcome this disadvantage, the solution temperature may be increased, the solution may be stirred with an agitation blade, or ultrasonic cleaning may be executed with an organic solvent that can dissolve a target resist well.

The obtained metal structure is closed on the plated side, so a metal substrate having a through-hole can be manufactured through dissolution with an acid aqueous solution or polishing.

In the resist pattern formation step for manufacturing the metal substrate having a through-hole, it is also possible that a fine concave pattern is formed to prepare a metal substrate having a fine convex pattern, and then plating is executed one more time to thereby manufacture a metal substrate having a through-hole. In this case, the metal structure having a fine convex pattern can be reused as the original pattern, and a production cost for the metal substrate having a through-hole can be saved.

Likewise, a resin-made through-type substrate can be manufactured, for example, through cast-molding of the obtained metal structure having a fine convex pattern. Any resin material can be used without particular limitations. Examples of the resist material include an acrylic resin, a polylactic acid, a polyglycolic acid, a styrene-based resin, a methacrylate/styrene copolymer resin (MS resin), a polycarbonate resin, a polyester resin such as polyethylene terephthalate, a polyvinyl alcohol resin, an ethylene/vinyl alcohol copolymer resin, a thermoplastic elastomer such as styrene-based elastomer, a vinyl chloride resin, a silicone resin such as polydimethyl siloxane, a vinyl acetate resin (for example, trade name: Exceval), and a polyvinyl butyral resin.

The through-type metal structure can be obtained by depositing a conductive film on a substrate beforehand or employing a conductive substrate in the fine convex resist pattern formation step without dissolving remaining patterns with an acid aqueous solution or polishing the surface after the removal of the fine convex resist pattern on the metal structure, leading to reduction in production cost of the through-type metal structure.

If a fine convex resist pattern is formed by use of the substrate having a conductive film formed thereon or a conductive substrate, the conductive film is exposed around the fine convex pattern. If plating is performed under this condition, metal is deposited only on the exposed conductive film to thereby produce a through-type metal structure. The adhesion between the conductive film on the substrate and the plated surface is low because an electric resistance of the conductive film is somewhat high due to the fine convex resist pattern. Thus, the through-type metal structure can be readily separated from the substrate.

There is no particular limitation on how to deposit a conductive film on the substrate. Preferably, evaporation and sputtering are used. As a conductive material for the conductive film, gold, silver, platinum, copper, nickel, and aluminum can be used. Any conductive substrate can be used without particular limitations, and a stainless steel, aluminum, or copper substrate may be used. The surface roughness of the substrate influences the surface roughness of the through-type metal structure, so it is preferred to subject the substrate to mirror polishing in accordance with the application and usage.

To form a through-hole with a desired depth, it is necessary to form a fine convex resist pattern with a desired height. A fine convex resist pattern can be formed with the desired height by repeating the resist layer formation and exposure several times, followed by development.

If the fine convex resist pattern height increases, there is a fear that the fine resist pattern falls down after development. To avoid such situation, for example, in the case of performing resist layer formation and exposure twice, two masks are used to set the dimension of a lower fine convex resist pattern larger than that of an upper fine convex resist pattern to thereby prevent the fine resist pattern from falling down.

Further, assuming that the through-hole has multistage structure, for example, in the case of performing resist layer formation and exposure twice, two kinds of masks are used to form lower and upper fine convex resist patterns of different shapes.

To realize a desired positional relation between the lower fine convex resist pattern and the upper fine convex resist pattern as planned, precise positioning should be carried out upon the exposure with a mask.

Examples of a positioning method include a method of cutting the substrate and the mask at the same positions and securing these in position with pins, a method of determining a position with a laser interferometer, and a method of marking the substrate and the mask at the same positions and adjusting positions with an optical microscope.

The method of adjusting the position with an optical microscope puts a position mark on the substrate by photolithography and a position mark on the mask with a laser printer. This method is effective in that an accuracy of 5 µm or less is realized even with manual operations by use of an optical microscope.

If the fine convex resist pattern height increases, there is a fear that the dimension of an upper fine convex resist pattern is smaller than that of a lower one in the developing step. In the case of forming plural resist layer, it is preferable to form resists of different sensitivities through several steps at the time of forming each resist layer in some cases. In this case, for example, a resist of an upper layer may be set to have higher sensitivity than that of a lower layer.

A light source for exposure is preferably UV light or laser light the plant cost of which is low. The Synchrotron orbital radiation that enables the large exposure depth requires a high plant cost. Thus, the through-type metal structure is high in price and impractical in industrial term.

A dimensional accuracy of the through-hole width of the through-type metal structure is preferably ±0.5 to 10% from the viewpoint of ease of reproduction in industrial term.

In the device for producing a microsphere with use of a metal substrate having a through-hole, if a partially or completely transparent plate is provided across a channel of a continuous phase so as to observe produced microspheres at least in a given portion of the continuous-phase side throughhole outlet, a microsphere production speed can be precisely controlled.

In particular, if a glass or plastic transparent plate is provided, it is possible to monitor whether or not microspheres are normally produced within a pressure range for microsphere production, through an external optical reader such as a CCD camera, and to precisely control the microsphere production speed in accordance with change in solution sending pressure for a disperse phase.

EXAMPLES

Hereinafter, the manufacturing method of a metal substrate having a through-hole according to the present invention is described in detail with reference to the drawings. The present invention is specifically described based on examples, but the present invention is not limited to the examples.

The manufacturing method of a metal substrate having a through-hole according to the present invention is described below in detail with reference to the drawings.

[First Manufacturing Method]

Referring first to FIG. 1A, an organic-material-based resist (based on "PMER N-CA3000PM" available from TOKYO OHKA KOGYO CO., LTD.) was applied onto the substrate 1 to form a resist layer 2.

Figure 1B:
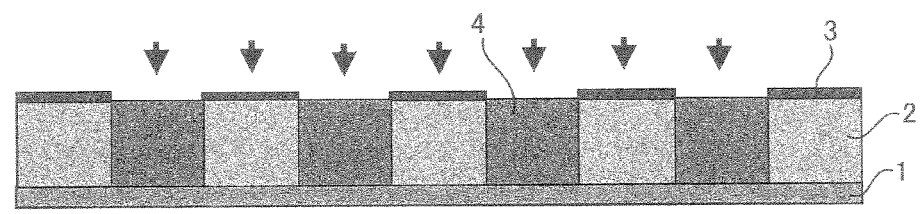
FIG. 1B is a schematic diagram of a manufacturing process of a metal substrate having a through-hole according to the present invention.

Referring to FIG. 1B, the resist layer 2 was subjected to exposure (wavelength of 365 nm and exposure amount of 300 mJ/cm$^2$) with the mask 3 by use of a UV exposure device ("PLA-501F" available from CANON Inc.).

Figure 1C:
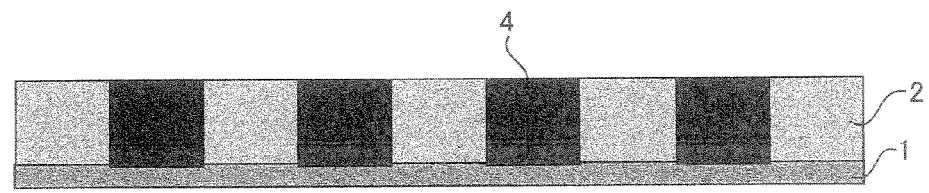
FIG. 1C is a schematic diagram of a manufacturing process of a metal substrate having a through-hole according to the present invention.

Referring to FIG. 1C, the resist layer 2 was subjected to heat treatment with a hot plate (100° C.×4 min).

Figure 1D:
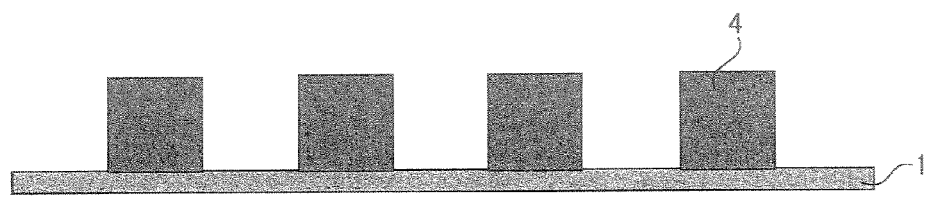
FIG. 1D is a schematic diagram of a manufacturing process of a metal substrate having a through-hole according to the present invention.

As shown in FIG. 1D, the substrate 1 having the resist layer 2 was subjected to development to form the resist pattern 4 on the substrate 1 (developer: "PMER developer P-7G" available from TOKYO OHKA KOGYO CO., LTD.).

Figure 1E:
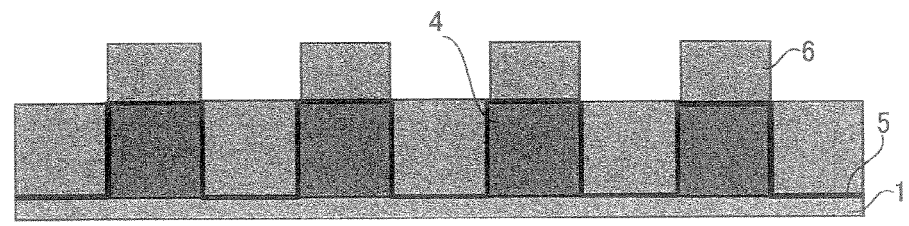
FIG. 1E is a schematic diagram of a manufacturing process of a metal substrate having a through-hole according to the present invention.

As shown in FIG. 1E, the surface of the substrate 1 having the resist pattern 4 was subjected to evaporation or sputtering to thereby deposit the conductive film 5 made of nickel on the resist pattern surface. In this step, platinum, silver, gold, copper, aluminum, or the like can be deposited instead.

Next, the substrate 1 having the resist pattern 4 was immersed into a plating solution to perform electro-plating to thereby form the metal structure (hereinafter also referred to as nickel structure) 6 between the resist patterns. In this step, copper, gold, or the like may be deposited instead.

Figure 1F:
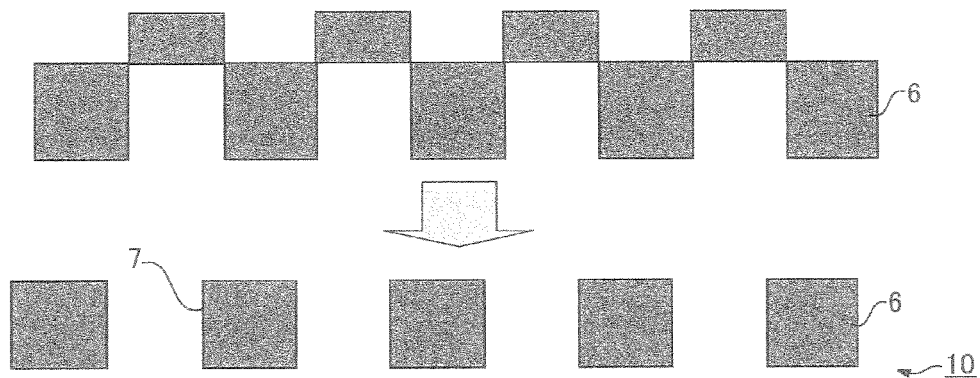
FIG. 1F is a schematic diagram of a manufacturing process of a metal substrate having a through-hole according to the present invention.

As shown in FIG. 1F, the nickel structure 6 peeled off of the substrate 1 was immersed into a solution to remove a resist adhering thereto. In this way, the nickel structure 6 was completed (solution: "CLEAN STRIP MF", available from TOKYO OHKA KOGYO CO., LTD.). Next, the plated side of the nickel structure 6 was polished to obtain the metal substrate 10 having the through-hole 7.

[Second Manufacturing Method]

Figure 2A:
FIG. 2A is a schematic diagram of a manufacturing process of a metal substrate having a through-hole according to the present invention.

Referring to FIG. 2A, the substrate 1 surface was first subjected to evaporation or sputtering to deposit the nickel-made conductive film 5. In this step, platinum, silver, gold, copper, aluminum, or the like can be deposited instead. Alternatively, a conductive substrate such as an aluminum substrate can be used. Next, an organic-material-based resist (based on "PMER N-CA3000PM" available from TOKYO OHKA KOGYO CO., LTD.) was applied onto the substrate 1 having the conductive film 5 to form a first resist layer 21.

Figure 2B:
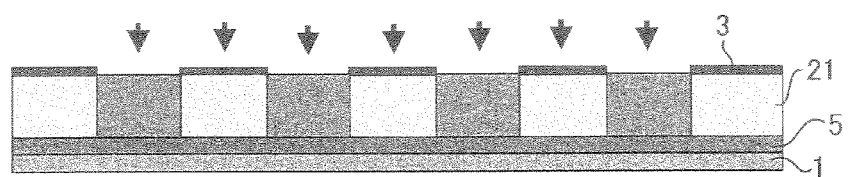
FIG. 2B is a schematic diagram of a manufacturing process of a metal substrate having a through-hole according to the present invention.

Referring to FIG. 2B, the first resist layer 21 was subjected to exposure (wavelength of 365 nm and exposure amount of 300 mJ/cm$^2$) with the mask 3 by use of a UV exposure device ("PLA-501F" available from CANON Inc.).

Upon the exposure, alignment exposure for adjusting a positional relation between the substrate and the mask was executed by use of positioning optical microscope of the UV exposure device such that the resist pattern of the first resist layer 21 and a second resist pattern as described later are secured in predetermined positions.

Figure 2C:
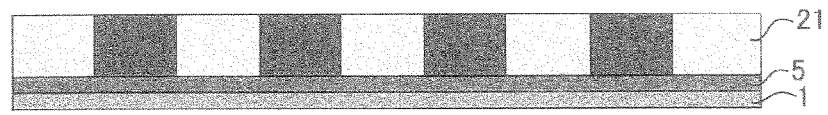
FIG. 2C is a schematic diagram of a manufacturing process of a metal substrate having a through-hole according to the present invention.

Referring to FIG. 2C, the first resist layer 21 was subjected to heat treatment with a hot plate (100° C.×4 min).

Figure 2D:
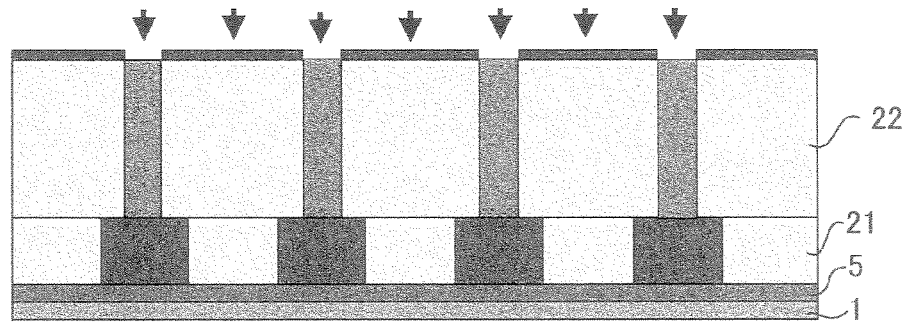
FIG. 2D is a schematic diagram of a manufacturing process of a metal substrate having a through-hole according to the present invention.

Referring to FIG. 2D, an organic-material-based resist (based on "PMER N-CA3000PM" available from TOKYO OHKA KOGYO CO., LTD.) was applied onto the substrate 1 having the first resist layer 21 to form a second resist layer 22. Next, the second resist layer 22 was subjected to exposure (wavelength of 365 nm and exposure amount of 300 mJ/cm$^2$) with the mask 3 by use of a UV exposure device ("PLA-501F" available from CANON Inc.).

Upon the exposure, alignment exposure for adjusting a positional relation between the substrate and the mask was executed by use of positioning optical microscope of the UV exposure device such that the resist pattern of the first resist layer 21 and the resist pattern of the second resist layer 22 are secured in predetermined positions.

Figure 2E:
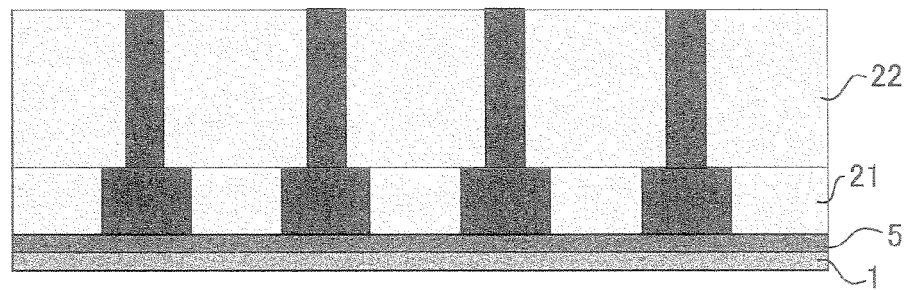
FIG. 2E is a schematic diagram of a manufacturing process of a metal substrate having a through-hole according to the present invention.

Referring to FIG. 2E, the second resist layer 22 was subjected to heat treatment with a hot plate (100° C.×4 min).

Figure 2F:
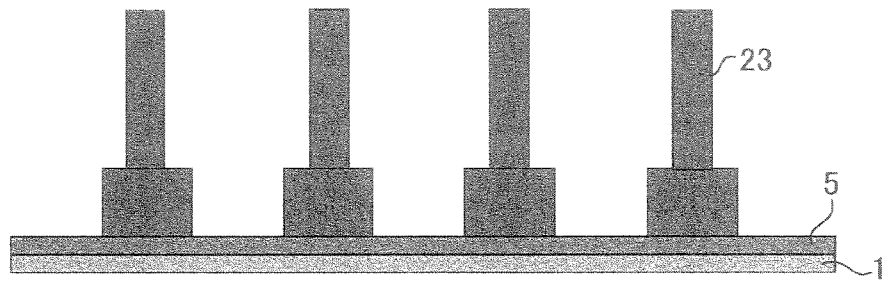
FIG. 2F is a schematic diagram of a manufacturing process of a metal substrate having a through-hole according to the present invention.

As shown in FIG. 2F, the substrate 1 having a resist layer composed of the first resist layer 21 and the second resist layer 22 was subjected to development to form a resist pattern 23 on the substrate 1 (developer: "PMER developer P-7G" available from TOKYO OHKA KOGYO CO., LTD.).

Figure 2G:
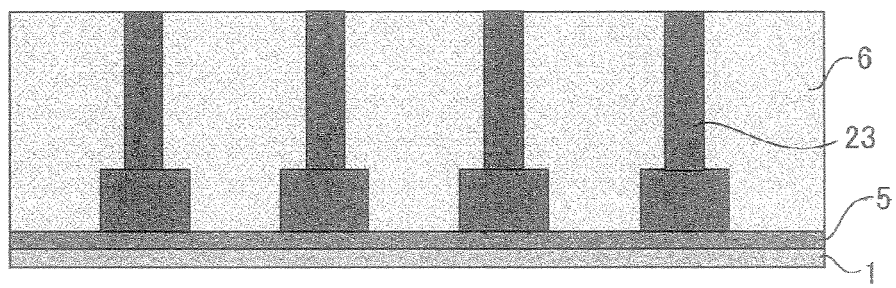
FIG. 2G is a schematic diagram of a manufacturing process of a metal substrate having a through-hole according to the present invention.

As shown in FIG. 2G, the substrate 1 having the resist pattern 23 was immersed into a plating solution to perform electro-plating to selectively deposit metal only between the resist patterns 23 to thereby form the metal structure (hereinafter referred to as nickel structure) 6. In this step, copper, gold, or the like may be deposited instead.

Figure 2H:
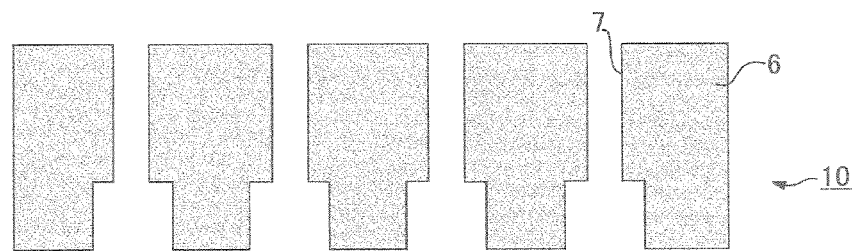
FIG. 2H is a schematic diagram of a manufacturing process of a metal substrate having a through-hole according to the present invention.

As shown in FIG. 2H, the nickel structure 6 peeled off of the substrate 1 was immersed into a solution to remove a resist adhering thereto. In this way, the metal substrate 10 having the through-hole 7 was completed (solution: "CLEAN STRIP MF", available from TOKYO OHKA KOGYO CO., LTD.).

[Production of Metal Substrate Having Through-Hole A]

In accordance with the process of FIGS. 1A to 1F, the resist application was repeated once to form a resist layer, and execute exposure, heat treatment, and development. Then, a through-type metal substrate having 60,000 through-holes measuring 10 μm (length)×20 μm (width)×100 μm (depth) was manufactured with a metal plate measuring 40 mm (length)×40 mm (width)×100 μm (thickness) as shown in FIGS. 4A to 4C. FIG. 4A is a top view of the metal substrate having a through-hole, FIG. 4B is a side view thereof, and FIG. 4C is a table of the number of through-holes.

Despite the through-type metal structure thickness as small as 100 μm, fine through-holes can be kept without deforming, and there is no problem about handling property. If the through-type metal structure is used, microspheres can be produced under high-pressure and high-temperature conditions.

A contact angle to the water was measured in the air with "CA-DT/A type" available from KYOWA INTERFACE SCIENCE CO. LTD. The measured angle was 88°.

Figure 5:
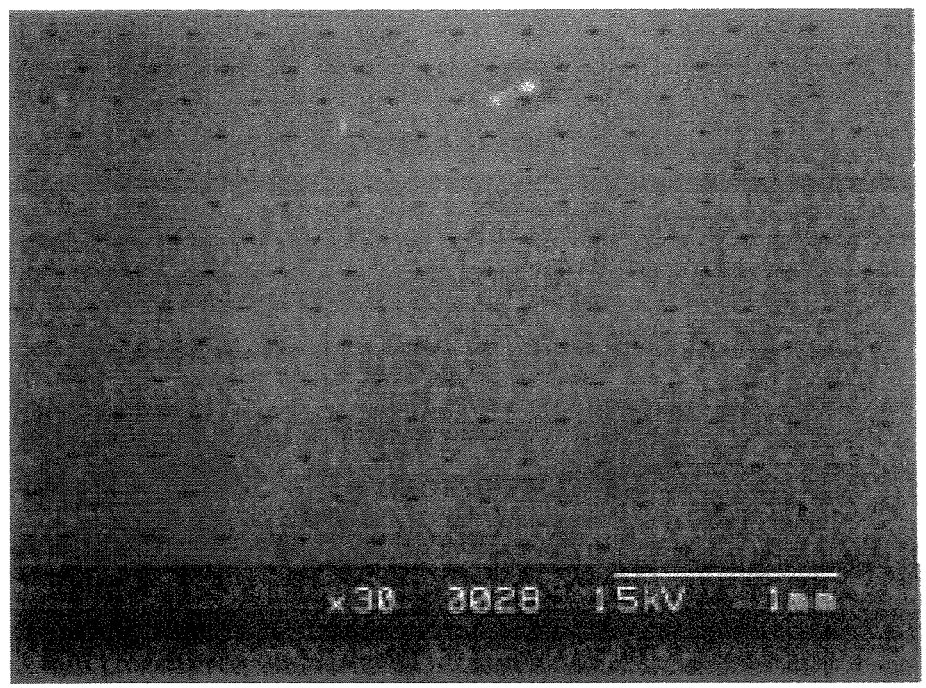
FIG. 5 shows an outer appearance and fine structure of a through-type metal structure observed with a SEM.
Figure 6:
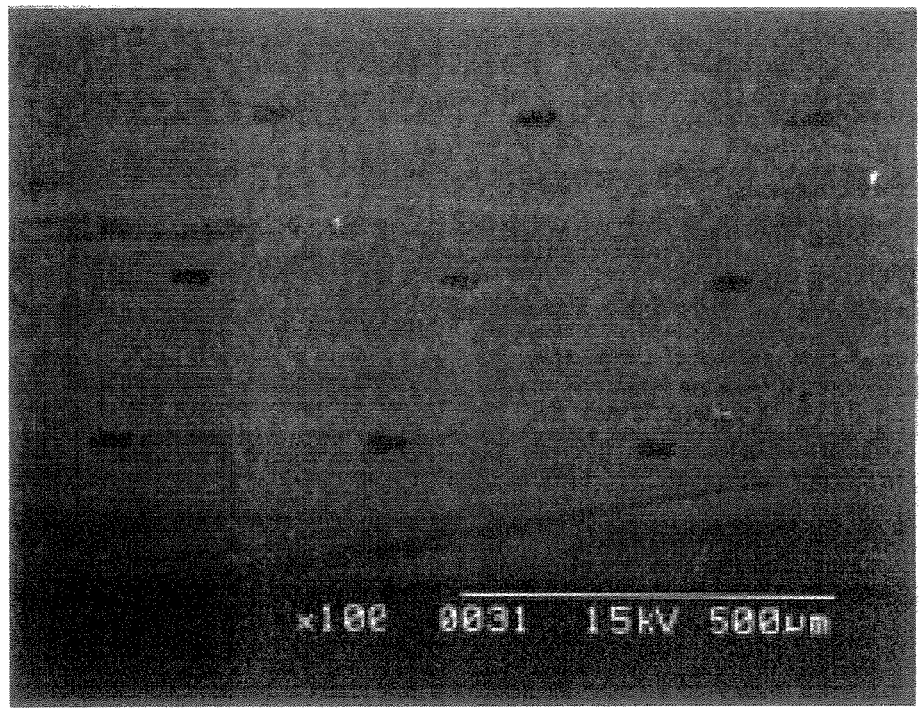
FIG. 6 shows an outer appearance and fine structure of a through-type metal structure observed with a SEM.
Figure 7:
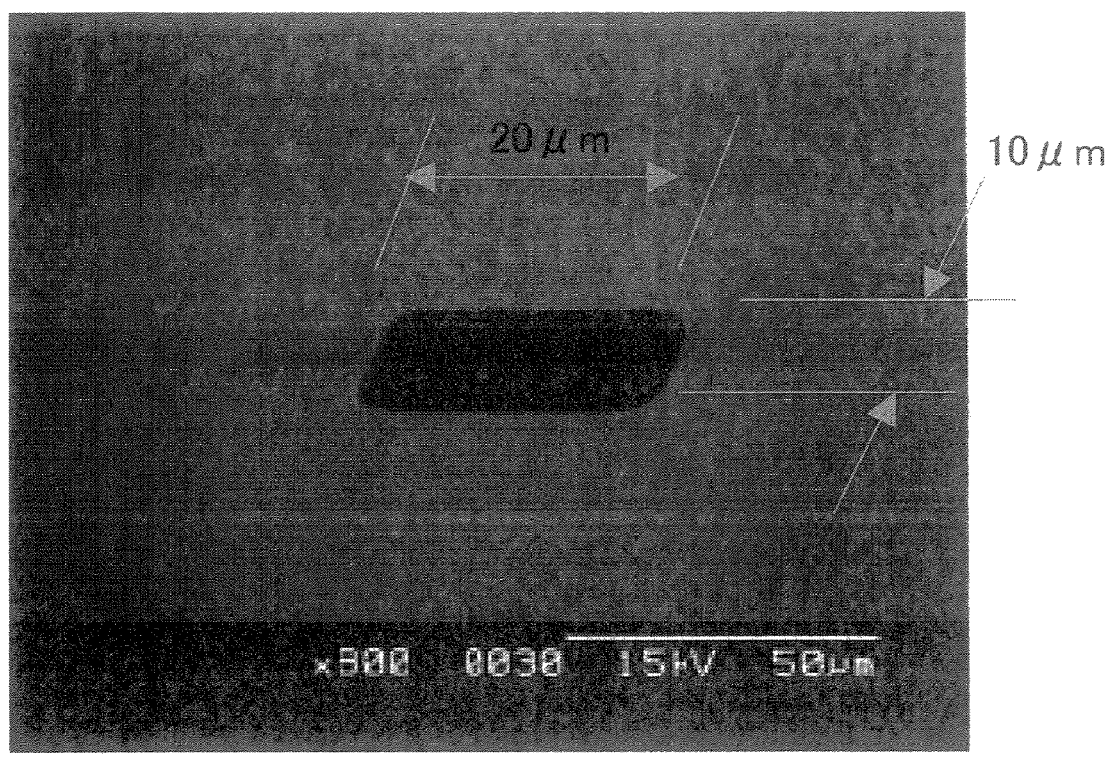
FIG. 7 shows an outer appearance and fine structure of a through-type metal structure observed with a SEM.

FIGS. 5, 6, and 7 show the fine structure of a through-type observed with a SEM. These photographs of the fine structure are taken from above the metal structure having a through-hole with different zoom factors. In the fine structure photographs, black portions correspond to through-holes.

[Production of Metal Substrate Having Through-Hole B]

In accordance with the process of FIGS. 2A to 2H, the resist application was repeated once to form a first resist layer, and execute exposure, heat treatment, and development on each layer. Then, the resist application was carried out once more to form a second resist layer and execute exposure and heat treatment. Then, a through-type metal substrate having 60,000 through-holes measuring 10 μm (length)×40 μm (width)×150 μm (depth) was manufactured with a metal plate measuring 40 mm (length)×40 mm (width)×300 μm (thickness) as shown in FIGS. 8A to 8C. FIG. 8A is a top view of the metal substrate having a through-hole, FIG. 8B is a side view thereof, and FIG. 8C is a table of the number of through-holes.

Despite the hole depth of the through-type metal structure as large as 300 μm, a metal substrate having a desired hole size can be obtained without destruction of patterns by performing multistage patterning for preventing the resist pattern from falling down.

A contact angle to the water was measured in the air with "CA-DT/A type" available from KYOWA INTERFACE SIENCE CO. LTD. The measured angle was 86°.

The metal substrate having a through-hole B is an example of the multistage structure, and two through-hole sizes of 10×40 μm and 30×60 μm are set.

[Production of Metal Substrate Having a Through-Hole C]

In accordance with the process of FIGS. 2A to 2H, the resist application was repeated once to form a first resist layer, and execute exposure, heat treatment, and development on each layer. Then, the resist application was carried out once more to form a second resist layer and execute exposure and heat treatment. Then, a through-type metal substrate having 60,000 through-holes measuring 20 μm (length)×20 μm (width)×20 μm (depth) on the upper side (continuous phase side) and 20 μm (length)×20 μm (width)×150 μm (depth) on the lower side (disperse phase side) was manufactured with a metal plate measuring 40 mm (length)×40 mm (width)×170 μm (thickness) as shown in FIGS. 9A to 9C. FIG. 9A is a top view of the metal substrate having a through-hole, FIG. 9B is a side view thereof, and FIG. 9C is a table of the number of through-holes.

The manufactured metal substrate having a through-hole was subjected to surface modification through evaporation with an EB evaporator (type: HP-1010F, available from ULVAC, Inc.) to thereby deposit an SiO$_2$ film up to the thickness of 200 nm. A contact angle to the water was measured in the air with "CA-DT/A type" available from KYOWA INTERFACE SIENCE CO. LTD. The measured angle was 18°.

In the metal substrate having a through-hole C, a through-hole is set to the multistage-structure for improving the microsphere production efficiency. This structure corresponds to the structure of the FIG. 3A.

[Production of Metal Substrate Having Through-Hole D]

In accordance with the process of FIGS. 2A to 2H, the resist application was repeated once to form a first resist layer, and execute exposure, heat treatment, and development on each layer. Then, the resist application was carried out once more to form a second resist layer and execute exposure and heat treatment. Then, a through-type metal substrate having 60,000 through-holes measuring 10 μm (length)×10 μm (depth) on the upper side (continuous phase side, continuous to the lower side) and 10 μm (length)×15 μm (width) (elliptical)×150 μm (depth) on the lower side (disperse phase side) was manufactured with a metal plate measuring 40 mm (length)×40 mm (width)×170 μm (thickness) as shown in FIGS. 10A to 10C. FIG. 10A is a top view of the metal substrate having a through-hole, FIG. 10B is a side view thereof, and FIG. 10C is a table of the number of through-holes.

The manufactured metal substrate having a through-hole was subjected to surface modification through evaporation with an EB evaporator (type: HP-1010F, available from ULVAC, Inc.) to thereby deposit an SiO$_2$ film up to the thickness of 200 nm. A contact angle to the water was measured in the air with "CA-DT/A type" available from KYOWA INTERFACE SIENCE CO. LTD. The measured angle was 21°.

In the metal substrate having a through-hole C, a through-hole is set to the multistage-structure for improving the microsphere production efficiency. This structure corresponds to the structure of the FIG. 3C.

[Production Water-in-Oil Type Monodisperse Microparticle with Use of Metal Substrate Having Through-Hole A]

As a substrate, the metal substrate A was set in a producing device as described below, and a production test of water-in-oil type monodisperse microparticles was executed under the condition that a disperse phase (water) is pure water and a continuous phase (oil) is triolein. Since the contact angle of the metal substrate to the water was as large as 88°, pure water as a disperse phase (water) was isolated at the outlet of a fluid channel, and an emulsion of uniform pure-water particle size could be produced A result of measuring a particle size with a particle size measurement device (type: PAR-III available from OTSUKA ELECTRONICS CO., LTD.) shows that an average particle size is 41.8 microns and coefficient of variation of 3.0%. As apparent from this, an emulsion including extremely uniform particles can be produced.

Upon the production of an emulsion, a process for separating particles from the metal substrate was captured with a CCD camera. As a result of checking particle production efficiency, 10 particles are produced per second.

[Production Water-In-Oil Type Monodisperse Microparticle with Use of Metal Substrate Having Through-Hole B]

As a substrate, the metal substrate B was set in a producing device as described below, and a production test of water-in-oil type monodisperse microparticles was executed under the condition that a disperse phase (water) is pure water and a continuous phase (oil) is triolein. Since the contact angle of the metal substrate to the water was as large as 86°, pure water as a disperse phase (water) was isolated at the outlet of a fluid channel, and an emulsion of uniform pure-water particle size could be produced. A result of measuring a particle size with a particle size measurement device (type: PAR-III available from OTSUKA ELECTRONICS CO. LTD.) shows that an average particle size is 34.1 microns and coefficient of variation of 2.5%. As apparent from this, an emulsion including extremely uniform particles can be produced.

Upon the production of an emulsion, a process for separating particles from the metal substrate was captured with a CCD camera. As a result of checking particle production efficiency, 15 to 20 particles are produced per second, and a through-hole having a larger ratio of length to width can produce a larger particle with a higher ability to isolate a particle.

[Production Water-In-Oil Type Monodisperse Microparticle with Use of Metal Substrate Having Through-Hole C]

As a substrate, the metal substrate C was set in a producing device as described below, and a production test of water-in-oil type monodisperse microparticles was executed under the condition that a disperse phase (oil) is soy oil and a continuous phase (water) is pure water. Since the contact angle of the metal substrate to the water was as small as 18°, the soy oil as a disperse phase (oil) was isolated at the outlet of a fluid channel, and an emulsion of uniform soy-oil particle size could be produced. A result of measuring a particle size with a particle size measurement device (type: PAR-III available from OTSUKA ELECTRONICS CO., LTD.) shows that an average particle size is 30.7 microns and coefficient of variation of 2.0%. As apparent from this, an emulsion including extremely uniform particles can be produced.

Upon the production of an emulsion, a process for separating particles from the metal substrate was captured with a CCD camera. As a result of checking particle production efficiency, 80 to 90 particles are produced per second, and a through-hole having a hole size on the fluid channel outlet side, which is larger than that of a through-hole of the substrate, can more easily guide a continuous phase to the outlet of the fluid channel and offer a smaller particle with a much higher ability to isolate a particle.

[Production Water-In-Oil Type Monodisperse Microparticle with Use of Metal Substrate Having Through-Hole D]

As a substrate, the metal substrate D was set in a producing device as described below, and a production test of water-in-oil type monodisperse microparticles was executed under the condition that a disperse phase (oil) is soy oil and a continuous phase (water) is pure water. Since the contact angle of the metal substrate to the water was as small as 21°, the soy oil as a disperse phase (oil) was isolated at the outlet of a fluid channel, and an emulsion of uniform soy-oil particle size could be produced. A result of measuring a particle size with a particle size measurement device (type: PAR-III available from OTSUKA ELECTRONICS CO., LTD.) shows that an average particle size is 28.6 microns and coefficient of variation of 1.5%. As apparent from this, an emulsion including extremely uniform particles can be produced.

Upon the production of an emulsion, a process for separating particles from the metal substrate was captured with a CCD camera. As a result of checking particle production efficiency, 90 to 100 particles are produced per second, and a through-hole continuous with an adjacent through-hole with a hole size on the fluid channel outlet side, which is larger than that of a through-hole of the substrate, can more easily guide a continuous phase to the outlet of the fluid channel and offer a smaller particle with a much higher ability to isolate a particle.

[Structural Example of Device for Producing Microsphere]

Figure 11:
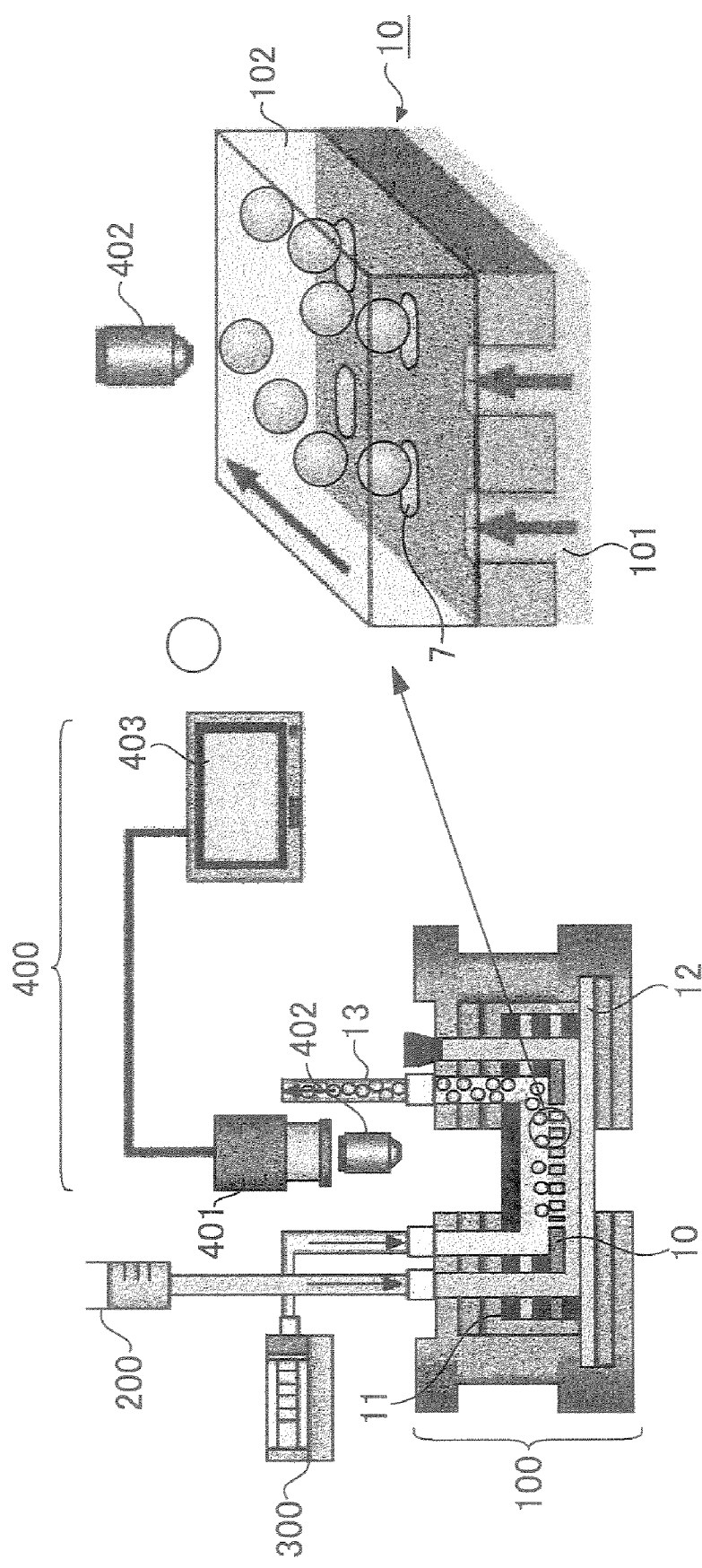
FIG. 11 is a schematic diagram of a device for producing a microsphere.

FIG. 11 shows a structural example of the device for producing a microsphere. The metal substrate having a through-hole 10 is secured in a MC module 100. Plural spacers 11 and plates 12 are assembled into the MC module 100. The plate 12 is, for example, a glass plate. In the MC module 100, a liquid-tight first channel 101 for supplying a disperse phase in a reservoir 200 (tank) provided above the channel is formed below the metal substrate 10 by forming the plate 12 into a ring shape. In addition, a liquid-tight second channel 102 for supplying a continuous phase and an emulsion from a pump 300 provided on the upper side is formed above the metal substrate 10 by forming the plate 12 into a ring shape. It is possible to monitor whether or not microspheres are normally produced in the second channel 102 through an objective lens 402 with an external optical reader such as a CCD camera 401, and to precisely control the microsphere production speed in accordance with change in driving pressure. An image taken by the CCD camera 401 is displayed on a monitor 403. In the case of producing microspheres with the thus-structured device, a disperse phase in the reservoir 200 is supplied to the first channel 101 at a predetermined pressure, and at the same time, the pump 300 supplies a continuous phase to the second channel 102 at a predetermined pressure. Since an inner pressure of the first channel 101 is generally set higher than that of the second channel 102 (in general, about 0.5 to 2 KPa), so the disperse phase in the first channel 101 is extruded through the through-hole 7 of the metal substrate 10, and produced microspheres are dispersed in the continuous phase to thereby produce emulsion. The produced emulsion is transferred to the reservoir through a pipe 13.

INDUSTRIAL APPLICABILITY

A process for producing a microsphere according to the present invention is applicable to production of an emulsion employed in the food industry, production of medicine and cosmetic, etc., an emulsion for DDS (drug delivery system), a microcapsule, an ion exchange resin, a chromatography carrier, or the like.

The invention claimed is:
1. A process for producing a microsphere, comprising:
separating a disperse phase from a continuous phase by a substrate having a through-hole; and
extruding the disperse phase into the continuous phase through the through-hole,
wherein at least one metal substrate is used, the metal substrate comprising a through-hole, with a width of 0.5 to 500 μm, a depth of 10 μm to 6000 μm, a ratio of the width to the depth of the through-hole (width/depth) of 1 to 1/30 (1/1 to 1/30), and a recess is around an opening of the through-hole on the side where a microsphere is formed.

2. The process of claim 1, wherein the metal substrate employed in the process is subjected to chemical surface treatment and/or physical surface treatment.

3. The process of claim 1, wherein the through-hole formed in the metal substrate has a multistage structure.

4. The process of claim 1, wherein a plurality of the metal substrates are employed in the process.

5. The process of claim 1, wherein the metal substrate employed in the process comprises through-holes of two or more different shapes.

6. The process of claim 1, wherein in the process a support plate supporting the substrate is formed on at least one side of the metal substrate.

7. A device for producing a microsphere, comprising:
   a case including a first plate, a substrate comprising a through-hole, and a second plate, which are spaced out in the case;
   a first channel through which a disperse phase flows and which is formed between the first plate and the substrate having a through-hole;
   a second channel through which a bed including a continuous phase and a microsphere flows and formed between the substrate having a through-hole and the second plate,
   wherein the substrate is a metal substrate comprising a through-hole, with a width of 0.5 to 500 µm a depth of 10 µm to 6000 µm, a ratio of the width to the depth of the through-hole (width/depth) of 1 to 1/30 (1/1 to 1/30), and a recess formed around an opening of the through-hole on a side where a microsphere is formed.

8. The device of claim 7, wherein at least a part of the first plate and/or the second plate is formed of a transparent material.

* * * * *